United States Patent
Adsul et al.

(10) Patent No.: US 11,407,974 B2
(45) Date of Patent: *Aug. 9, 2022

(54) METHOD FOR PREPARATION AND SCREENING OF FUNGAL MUTANT WITH HIGH HYDROLYTIC ACTIVITY AND CATABOLITE DEREPRESSED CHARACTER

(71) Applicants: INDIAN OIL CORPORATION LIMITED, Mumbai (IN); DEPARTMENT OF BIOTECHNOLOGY, New Delhi (IN)

(72) Inventors: Mukund Adsul, Faridabad (IN); Simranjeet Kaur Sandhu, Faridabad (IN); Reeta Rani Singhania, Faridabad (IN); Jitendra Kumar Saini, Faridabad (IN); Anshu Shankar Mathur, Faridabad (IN); Ravi Prakash Gupta, Faridabad (IN); Deepak Kumar Tuli, Faridabad (IN); Suresh Kumar Puri, Faridabad (IN); Sankara Sri Venkata Ramakumar, Faridabad (IN)

(73) Assignees: INDIAN OIL CORPORATION LIMITED, Mumbai (IN); DEPARTMENT OF BIOTECHNOLOGY, New Delhi (IN)

( * ) Notice: Subject to any disclaimer, the term of this patent is extended or adjusted under 35 U.S.C. 154(b) by 156 days.

This patent is subject to a terminal disclaimer.

(21) Appl. No.: 16/584,785

(22) Filed: Sep. 26, 2019

(65) Prior Publication Data

US 2020/0102621 A1 Apr. 2, 2020

(30) Foreign Application Priority Data

Sep. 27, 2018 (IN) .............. 201821036496

(51) Int. Cl.
| | | |
|---|---|---|
| *C12N 1/14* | (2006.01) |
| *C12N 15/01* | (2006.01) |
| *C12N 9/42* | (2006.01) |
| *C12P 19/02* | (2006.01) |
| *C12P 19/12* | (2006.01) |
| *C12P 19/14* | (2006.01) |
| *C12R 1/80* | (2006.01) |

(52) U.S. Cl.
CPC .............. *C12N 1/145* (2021.05); *C12P 19/14* (2013.01); *C12R 2001/80* (2021.05); *C12Y 301/08002* (2013.01); *C12Y 302/01004* (2013.01); *C12Y 302/01015* (2013.01); *C12Y 302/01021* (2013.01); *C12Y 302/01032* (2013.01); *C12Y 302/01055* (2013.01)

(58) Field of Classification Search
None
See application file for complete search history.

(56) References Cited

U.S. PATENT DOCUMENTS

2014/0036384 A1 2/2014 Zheng et al.

FOREIGN PATENT DOCUMENTS

| CN | 102559506 A | 7/2012 |
| CN | 103045484 A | 4/2013 |

OTHER PUBLICATIONS

Bose, J., Methods Mol. Biol. 1373:111-115, 2016 (Year: 2016).*
Randhawa et al., Biotechnol. Biofuels 11:15, 2018, 22 pages (Year: 2018).*
Soam et al. "Global warming potential and energy analysis of second generation ethanol production from rice straw in India" Applied Energy 184 (Apr. 2016) 353-364.

* cited by examiner

*Primary Examiner* — David Steadman
(74) *Attorney, Agent, or Firm* — Maschoff Brennan

(57) ABSTRACT

The present invention relates to a mutant fungal strain of *Penicillium funiculosum* 'MRJ-16' characterized by the ability to produce high titer of enzyme mixture comprising FPase, CMCase, Cellobiase, β-glucosidase, endoglucanase, α-L arabinofuranosidase, β-xylosidase, xylanase, pectinase, cellobiohydrase and oxidases and produce enzymes in the presence of a catabolite repressor molecule like glucose and/or xylose. The titer of enzyme mixture produced using mutant fungal strain MRJ-16 is at least two fold higher than naive *Penicillium funiculosum* strain NCIM 1228, when used in a fermentation process. The mutant strain 'MRJ-16' with high hydrolytic activity and catabolite derepressed character is having application in the method of degrading or saccharifying biomass to produce valuable products for example-bioethanol.

6 Claims, 1 Drawing Sheet

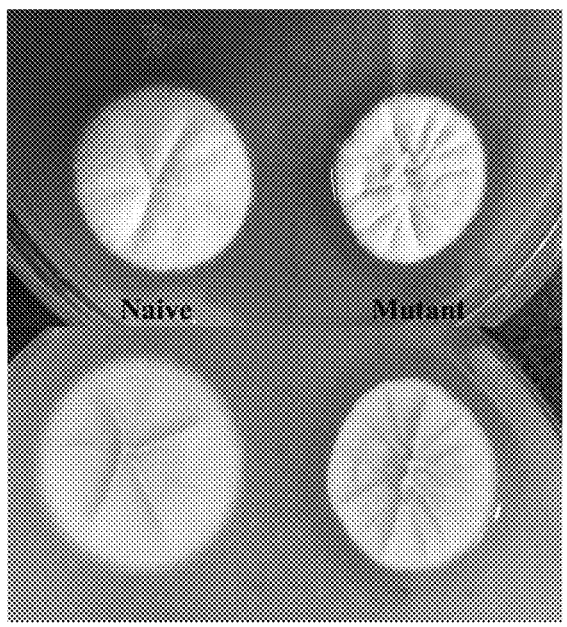

METHOD FOR PREPARATION AND SCREENING OF FUNGAL MUTANT WITH HIGH HYDROLYTIC ACTIVITY AND CATABOLITE DEREPRESSED CHARACTER

FIELD OF THE INVENTION

The present invention relates to a hyper-cellulolytic, catabolite derepressed mutant of ascomycetes fungus, *Penicillium funiculosum* NCIM 1228 strain. More particularly, the present invention relates to a mutant fungal strain of *Penicillium funiculosum* 'MRJ-16' with hyper-cellulolytic and catabolite derepressed activity, having ability to produce enzymes in the presence of catabolite repressor such as D-glucose. The present invention also relates to a process for preparing and screening the same.

BACKGROUND OF THE INVENTION

Enzymes remain a significant cost factor in cellulosic ethanol process. The development of economically viable enzyme production process with high enzyme productivity, specificity and cocktail mixture appropriate for the hydrolysis of lignocellulosic biomass can reduce the problem in commercialization of second generation biofuels. Second generation lignocellulosic biomass based biofuels are highly advantageous as the biomass is readily available, cheap and renewable. It has been stated by numerous researchers that ethanol derived from lignocellulosic biomass can decrease green house gas emission by more than 80% (Soam et al. 2016). Lignocellulosic biomass is a complex mixture of cellulose, hemicelluloses and lignin. These substrates have to undergo various pretreatment processes in order to improve the accessibility for enzymatic hydrolysis to release sugars for ethanol production. Sugars released after enzymatic hydrolysis can be converted into other platform chemicals such as butanol, methanol, dimethyl ether, succinic acid, fumaric acid, glutamic acid and sorbitol etc.

Lack of hyper cellulolytic microorganisms, less enzyme titer and high cost of growth media constituents are some of the major limiting factors that makes the process for biomass hydrolysis quite expensive. So, the reduction of overall enzyme production cost and development of industrially viable strain are the major goals of enzyme manufacturing industries. To economize the process, high titer of cellulolytic and hemicellulolytic enzymes, efficiency of enzyme cocktail for biomass hydrolysis, time required for enzyme production and handling of overall process are important area to focus.

Many fungal and bacterial species are efficient producers of cellulases enzymes but preferences have been given to the fungal microorganisms because of their ability to secrete complete cellulase system in the medium at high titer. Wild type fungal strains do not produce sufficient amount of cellulases enzymes required for efficient hydrolysis of lignocellulosic biomass and produce small amounts of β-glucosidase. Several efforts have been made to develop recombinant or mutant strains of ascomycetes filamentous fungi like *Trichoderma, Penicillium, Fusarium, Humicola* and *Aspergillus* species for industrial production of cellulases. Conventional mutational techniques have permitted the mutant strain of *Penicillium* to be selected for production of hyper-cellulases.

Mutagenesis is an extensive method to improve the efficiency of fungi to secrete cellulose degrading enzyme at high titer. Mutagenesis technique include physical mutagens like UV-light, gamma rays, X-rays, infra-red rays etc and chemical mutagens like methyl nitrosoguanidine, nitrous oxide, ethyl-methane-sulphonate, hydroxylamine, dimethyl sulphate etc. Jafari N et al (2017) has improved the cellulolytic activity of *Aspergillus niger* using UV-light, resulting in the mutant with two fold increase in filter paper activity (FPA). Similarly, cellulase and xylanase activities in *Penicillium verruculosum* 28K mutants were improved about 3-fold using four cycles of UV mutagenesis. The enzyme production was further improved by 2- to 3-fold in a two-stage fermentation process using wheat bran, yeast extract medium and microcrystalline cellulose as the inducer (Solov'eva I V et al. 2005). *Trichoderma atroviride* mutants were created by mutagenesis using N-methyl-N'-nitro-N-nitrosoguanidine (NTG) as well as UV-light by Kovacs and et al. (2008). These *T. atroviride* mutants (e.g. *T. atroviride* TUB F-1724) produce high levels of β-glucosidase and extracellular cellulases using pretreated willow. In another study, the catalytic efficiency and optimum pH of *T. reesei* endo-β-1, 4-glucanase II were improved by saturation mutagenesis followed by random mutagenesis and two rounds of DNA shuffling. The pH optimum of the variant (Q139R/L218H/W276R/N342T) was shifted from 4.8 to 6.2, while the enzyme activity was improved more than 4.5-fold (Qin Y et al. 2008).

US 2014/0363846 describes the process for cellulases enzyme production using fungal cells of genus *Myceliophthora* by submerged fermentation and soluble non cellulase-inducing carbon sources were used. Carbon sources used were glucose, glycerol, xylose, glucose: xylose (90:10), sucrose, glucose and inducing substrate like sophorose, gentibiose and cellobiose, molasses, fructose and glucose: fructose (50:50). Similar protein and Filter paper activity (FPU) was observed when glucose alone and with inducing substrate was used as carbon sources. Maximum of average 0.55 FPU/mg proteins was observed when xylose was used. Claimants of the patent mentioned about the variety of cellulases, hemicellulases, lignin degrading enzymes, estrases, swollenin, expansins and many more additional enzymes secreted by the *Myceliophthora thermophila* strain (ATCC No. 42464) used but didn't present any of the activity of above these in patent expect Filter paper activity.

CN103045484B mentioned the production of cellulases enzyme using *Penicillium decumbens* (CCTCC M2011195) mutant strain. A mutant strain was developed using UV irradiation and a chemical mutagen NTG (N-methyl-N'-nitro-N-nitrosoguanidine). The fermentation medium was composed of fishing xylose, wheat bran, microcrystalline cellulose, ammonium sulfate, potassium phosphate monobasic and magnesium salt. Enzyme activity obtained was filter paper 10 IU/ml, endoglucanase activity 30 IU/ml, exoglucanase activity 1. 5 IU/ml and β-glucosidase 8 IU/ml. The enzyme cocktail produced by the researchers will be insufficient if used for biomass hydrolysis because of low β-glucosidase titer in comparison to filter paper activity, thus more enzymes need to be doped. Furthermore, the choice of carbon source as fishing xylose and nitrogen source as wheat bran may makes this process rather uneconomical and non-sustainable.

Patent application no. CN102559506A (2013), *Penicillium oxalicum* CGMCC No. 4357 strain was isolated and identified to produce cellulases enzymes using corn stover flour as carbon source. They claim that the process of enzyme production was fast (7 days) with shaking cultured to reach peak endoglucanases, exoglucanases and β-glucosidase activity of 228. 17 IU/ml, 109. 90 IU/ml and 81.45 IU/ml respectively. Enzyme was used for corn stover straw saccharification at 9% (w/v) cellulose concentration; saccharification rate was calculated to be more than 80% when 25 ml of enzyme (50% of total volume) was used. The amount of enzyme used by the claimants is very high and substrate concentration is low, which is not economically viable for industrial scale process.

Hence, there is an urgent need for a fungal mutant strain which is sensitive to catabolite repression, easy to handle, can use cost effective carbon, nitrogen and mineral requirement and possess high titer enzyme production efficiency. The Penicillium funiculosum 'MRJ-16' mutant strain of the present invention produces a well-balanced cocktail mixture of β-glucosidase, endo-glucanases and exo-glucanase, resulting in desire performance in hydrolyzing lignocellulosic biomass. Other proteins which are vital for the hydrolysis of biomass are also secreted by this fungus.

OBJECTIVE OF THE PRESENT INVENTION

The primary object of the present invention is to provide a mutant fungal strain of Penicillium funiculosum 'MRJ-16' with hyper-cellulolytic and catabolite derepressed activity.

Another object of the present invention is to provide a process for preparing and screening the mutant fungal strain of Penicillium funiculosum 'MRJ-16'.

Yet another object of the present invention is to provide a process for degrading or saccharifying the biomass using the enzymes secreted by the mutant fungal strain of Penicillium funiculosum 'MRJ-16'.

Another object of the present invention is to provide a process for preparing high titer of cellulases and β-glucosidase for biomass hydrolysis in cost effective manner.

SUMMARY OF THE INVENTION

The present relates to a mutant fungal strain of Penicillium funiculosum 'MRJ-16' characterized by the ability to produce high titer of enzyme mixture comprising FPase, CMCase, Cellobiase, β-glucosidase, endoglucanase, α-L arabinofuranosidase, β-xylosidase, xylanase, pectinase, cellobiohydrase and oxidases and is having catabolite derepressed character.

In an embodiment of the present invention, the enzyme mixture produced by mutant fungal strain comprises cellulase and β-glucosidase.

In an embodiment of the present invention, the catabolite repressor molecule is glucose and/or xylose.

In an embodiment of the present invention, the titer of enzyme mixture produced by mutant fungal strain 'MRJ-16' is at least two fold higher than the titer of enzyme mixture produced by naive Penicillium funiculosum NCIM 1228 strain.

The present also relates to a method of preparing a mutant fungal strain comprising the steps of:
  (i) selecting and subjecting Penicillium funiculosum NCIM 1228 to aerobic culture media to prepare spore suspension of about 1×10$^6$ spore/mL;
  (ii) mutating spore suspension of step (i) by method selected from chemical mutagenesis, physical mutagenesis, a combination of both;
  (iii) screening mutant colonies with cellulolytic activity using screening media comprising amorphous cellulose in a concentration 0.1%-2% (w/w) and glucose in a concentration 0.1-4% (w/w).
  (iv) obtaining mutant fungal strain Penicillium funiculosum 'MRJ-16'.

In an embodiment of the present invention, the chemical mutagenesis in step (ii) of the process is carried out with ethyl methanesulfonate (EMS) or diethyl sulfate (DES) in concentration of about 10-50 µL/mL spore suspension or with both in 1:1 concentration for 15 hours under dark at room temperature.

In an embodiment of the present invention, the physical mutagenesis of step (ii) of the process is carried out with UV light of wavelength 254 nm for 2-5 minutes at a distance of 15 cm.

In an embodiment of the present invention, the chemical mutagenesis is followed by physical mutagenesis.

In an embodiment, the present invention relates to a process for the production of cellulase enzymes using Penicillium funiculosum 'MRJ 16' strain.

In an embodiment, the present invention relates to a method for degrading or saccharifying biomass using Penicillium funiculosum 'MRJ 16' strain.

DESCRIPTION OF THE ACCOMPANYING DRAWING

FIG. 1: Penicillium funiculosum NCIM 1228 (naive strain) and mutant colony on screening media plate

DETAILED DESCRIPTION OF THE INVENTION

The present invention relates to a mutant fungal strain derived from Penicillium funiculosum NCIM 1228, which can produce high titer of enzyme mixture using cheap growth components, having catabolite derepressed character, can produce enzymes in the presence of catabolite repressor molecule like glucose and/or xylose. Hence, present invention provides a commercially viable and sustainable process of enzyme cocktail preparation for the hydrolysis of pretreated lignocellulosic biomass, which is useful for the production of biofuels.

According to first aspect, the present invention provides a mutant fungal strain of Penicillium funiculosum 'MRJ-16' (MTCC Accession No. 25142 and date of deposition 12 Jun. 2017) characterized by the ability to produce high titer of enzyme mixture comprising FPase, CMCase, Cellobiase, β-glucosidase, endoglucanase, α-L arabinofuranosidase, β-xylosidase, xylanase, pectinase, cellobiohydrase and oxidases. In an embodiment of the present invention, the mutant fungal strain 'MRJ-16' produces enzyme mixture comprising β-glucosidase 62-64 IU/ml, Filter paper activity 6.2-6.4 FPU/ml, endoglucanase 92-98 IU/ml, α-L arabinofuranosidase 0.02 IU/ml, β-xylosidase 0.5-0.7 IU/ml, xylanase 212-235 IU/ml, pectinase 82-97 IU/ml and oxidases 4.65-5.04 IU/ml as shown in examples 8 and 9.

The naive strain of P. funiculosum NCIM 1228 shows catabolite repression on enzyme production i.e. it does not secrete enzymes in the presence of a catabolite repressor molecule like glucose and/or xylose. The present invention overcomes this limitation. According to second aspect, the present invention provides a mutant fungal strain of Penicillium funiculosum 'MRJ-16' having catabolite derepressed character. In an embodiment of the present invention, the P. funiculosum MRJ-16 cultured on fermentation media of examples 3 and 5 comprising glucose 3% (w/v), after 120 hours of fermentation process produce 1.39 FPU/ml and 21 IU/ml β-glucosidase (BGL). Hence, the titre of enzyme mixture is at least two to twenty two times higher as shown in Table 6.

According to third aspect, the present invention provides a method of preparing a mutant fungal strain comprising the steps of:

(i) selecting and subjecting *Penicillium funiculosum* NCIM 1228 to aerobic culture media to prepare spore suspension of about 1×10$^6$ spore/mL;
(ii) mutating spore suspension of step (i) by method selected from chemical mutagenesis, physical mutagenesis, a combination of both;
(iii) screening mutant colonies with cellulolytic activity using screening media comprising amorphous cellulose in a concentration 0.1%-2% (w/w) and glucose in a concentration 0.1-4% (w/w).
(iv) obtaining mutant fungal strain *Penicillium funiculosum* 'MRJ-16'.

In an embodiment of the present invention, the spore suspension of naive strain of *Penicillium funiculosum* NCIM 1228 is prepared in a sterile saline solution containing 0.1% Tween-80 from a 7 day old potato dextrose agar (PDA) culture grown at 30° C.

In an preferred embodiment of the present invention, the spore suspension of naive strain of *Penicillium funiculosum* NCIM 1228 is subjected to chemical mutagenesis with ethyl methanesulfonate (EMS) or diethyl sulfate (DES) in a concentration of about 10-50 µL/mL spore suspension or with both in 1:1 concentration for 15 hours under dark at room temperature.

In another embodiment of the present invention, the spore suspension of naive strain of *Penicillium funiculosum* NCIM 1228 is subjected to physical mutagenesis with UV light and/or NTG (N-methyl-N'-nitro-N-nitrosoguanidine) and/or EMS (Ethyl methanesulfonate). In a preferred embodiment, the spore suspension of parent strain NCIM 1228 is treated with UV light (254 nm, Philips TUV-30 W lamp) for 2-5 minutes at a distance of 15 cm in a wooden UV-box. In a preferred embodiment, the method comprises chemical mutagenesis followed by physical mutagenesis.

Selection of mutual fungal strain is carried out by visually selection on the basis of yellow pigmentation and measuring the amorphous cellulose hydrolyzed zone in the screening media. In a preferred embodiment of present invention, the process of screening mutant colonies with cellulolytic activity is carried out using solid media comprising amorphous cellulose ranging from 0.1% to about 2% (w/w) and a catabolite repressor molecule like glucose and or xylose in a concentration of about 0.1-4% (w/w). In an embodiment, the mutant colonies are selected by measuring the diameter of hydrolyzed zone surrounding the colonies. In a preferred embodiment, MRJ-16 produce wide clear zone with diameter of about 28-32 mm and the colony diameter of about 21-24 mm.

In an embodiment, the present invention relates to a process for the production of cellulase enzymes using the mutant strain of *Penicillium funiculosum* 'MRJ-16'. The process comprises culturing *Penicillium funiculosum* 'MRJ-16' strain in a culture medium comprising carbon source selected from the group consisting of rice straw, wheat straw, baggase or a mixture thereof. This is followed by collecting the cellulase enzymes from the culture medium. In a preferred embodiment, MRJ 16 mutant strain comprises cellulase enzymes comprising β-glucosidase 62-64 IU/ml, Filter paper activity 6.2-6.4 FPU/ml.

In an embodiment of the present invention, the enzymes produced by *Penicillium funiculosum* MRJ-16 mutant strain are used without any downstream process. Hydrolysis of 20% pre-treated lignocellulosic biomass such as acid pre-treated rice at pH 4-5, 50 mM citrate buffer, temperature 50° C. at enzyme loadings of 6 FPU/g of dry biomass leads to 60% glucan conversion in 48 hours. In a preferred embodiment, an enzyme loading of 6 FPU/g of dry biomass is either clear enzyme broth or enzyme broth without any downstream processing, as exemplified in Examples 10 and 11.

Following non-limiting examples are given by way of illustration for specific embodiments thereof and therefore should not be construed to limit the scope of the invention.

EXAMPLES

Example 1

Mutagenesis Procedure for Preparing Mutant Fungal Strain *Penicillium Funiculosum* MRJ-16

Spore suspension (approx. 1×10$^6$ Spore/mL) of naive strain was prepared in sterile saline containing 0.1% Tween-80 from a 7 day old Potato dextrose agar (PDA) culture grown at 30° C. Spore suspension was subjected to chemical mutagenesis by treating them with ethyl methanesulfonate (EMS) or diethyl sulfate (DES) of concentration about 10-50 µL/mL spore suspension or both at 1:1 concentration for 15 hours under dark at room temperature. This was followed by physical mutagenesis of suspension with UV light (254 nm, Philips TUV-30 W lamp) for 2-5 min at a distance of 15 cm in a wooden UV-box. The spore suspension after combined mutagenesis was spread (100 µL) onto screening media containing 0.3%-0.5% wt. amorphous cellulose and 0.5-3% glucose. The plates were incubated under dark at 30° C. for 4-6 days and colonies with cellulolytic activity were visually detected by observing a clear transparent halo surrounding the colonies. The obtained mutant colonies were counted and potential mutant colonies were identified on the basis of clear halo zone.

Example 2

Screening of an Efficient Mutant for Enzyme Production

The naive strain of *Penicillium funiculosum* NCIM 1228 was used to create mutants for enzyme production. Mutations were done using UV or NTG or EMS mutagens alone or all together. The mutant strains were obtained after repeated multi-stage mutagenesis process. Mutants were selected sequentially on specially designed media containing amorphous cellulose and glucose at different concentration from 1-4% (w/w) (screening media composition in table 1). Naive strain didn't hydrolyze amorphous cellulose in the presence of glucose. Mutant strain that hydrolyzes the amorphous cellulose in the presence of 3% glucose was selected after visualizing and measuring the hydrolyzed zone. Stability of mutant stain for enzyme production capability was tested for multiple cycles and then used for further study.

TABLE 1

| Screening media composition | | |
|---|---|---|
| S. No. | Chemical Components | Quantity (g/L) |
| 1 | Ammonium Sulphate | 1.4 |
| 2 | $KH_2PO_4$ | 2.0 |
| 3 | $MgSO_4 \cdot 7H_2O$ | 0.3 |
| 4 | $CaCl_2 \cdot 3H_2O$ | 0.3 |
| 5 | Urea | 0.3 |
| 6 | Tween-80 | 0.1 |
| 7 | Peptone | 0.25 |
| 8 | Yeast Extract | 0.10 |
| 9 | $ZnSO_4 \cdot 7H_2O$ | 0.0014 |

TABLE 1-continued

Screening media composition

| S. No. | Chemical Components | Quantity (g/L) |
|---|---|---|
| 10 | FeSO$_4$•7H$_2$O | 0.005 |
| 11 | MnSO$_4$•H$_2$O | 0.0016 |
| 12 | CoCl$_2$•6H$_2$O | 0.002 |
| 13 | Glucose | 15 |
| 14 | Amorphous cellulose | 1.5 |
| 15 | Agar | 20 |
| 16 | pH | 5.0 |

The visual observation of the *Penicillium funiculosum* NCIM 1228 (naive strain) and mutant (MRJ-16) cultured on screening media plate showed that in the presence of 3% glucose, naive stain do not produce clear zone and mycelia appear white till 10-13 days of incubation, while MRJ-16 started turning yellow before the onset of spores as shown in FIG. 1. More wrinkled surface was observed in case of MRJ-16 than naive strain. MRJ-16 produce wide clear zone with diameter 28 mm, the colony diameter of naive and MRJ-16 mutant strain was 25 mm and 21 mm respectively.

Example 3

Screening of an Efficient Mutant for Enzyme Production

The naive strain of *Penicillium funiculosum* NCIM 1228 was used to create mutants for enzyme production. Mutations were done using UV or NTG or EMS mutagens alone or all together. The mutant strains were obtained after repeated multi-stage mutagenesis process. Mutants were selected sequentially on specially designed media containing amorphous cellulose and glucose at different concentration from 1-4% (w/w) (screening media composition in table 2). Naive strain didn't hydrolyze amorphous cellulose in the presence of glucose. Mutant strain that hydrolyzes the amorphous cellulose in the presence of 4% glucose was selected after visualizing and measuring the hydrolyzed zone. Stability of mutant stain for enzyme production capability was tested for multiple cycles and then used for further study.

TABLE 2

Screening media composition

| S. No. | Chemical Components | Quantity (g/L) |
|---|---|---|
| 1 | Ammonium Sulphate | 2.4 |
| 2 | KH$_2$PO$_4$ | 3.0 |
| 3 | MgSO$_4$•7H$_2$O | 0.1 |
| 4 | CaCl$_2$•3H$_2$O | 0.1 |
| 5 | Urea | 0.2 |
| 6 | Tween-80 | 1.0 |
| 7 | Peptone | 0.5 |
| 8 | Yeast Extract | 1.0 |
| 9 | ZnSO$_4$•7H$_2$O | 0.005 |
| 10 | FeSO$_4$•7H$_2$O | 0.005 |
| 11 | MnSO$_4$•H$_2$O | 0.002 |
| 12 | CoCl$_2$•6H$_2$O | 0.002 |
| 13 | Glucose | 25 |
| 14 | Amorphous cellulose | 2.5 |
| 15 | Agar | 20 |
| 16 | pH | 5.5 |

The visual observation of the *Penicillium funiculosum* NCIM 1228 (naive strain) and mutant (MRJ-16) cultured on screening media plate showed that in the presence of 3% glucose, naive stain do not produce clear zone and mycelia appear white till 10-13 days of incubation, while MRJ-16 started turning yellow before the onset of spores. More wrinkled surface was observed in case of MRJ-16 than naive strain. MRJ-16 produce wide clear zone with diameter 32 mm, the colony diameter of naive and MRJ-16 mutant strain was 28 mm and 24 mm respectively.

Example 4

SNPs Analysis of Mutant Fungal Strain MRJ-16 and Naive Strain

The filtered paired end fastq files of sample M (mutant strain MRJ-16) were aligned to the sample V (naive strain) assembly using bowtie2 aligner. The mapping had an overall alignment rate of 95.38%. The alignment sequence map file was further sorted and indexed before the SNPs were predicted. The SNPs prediction was facilitated by samtools mpileup and bcftools view functions. VarFilter tool was used to filter the SNP sites with QUAL value greater than or equal to 100. There were a total of 1655 SNP sites observed in the sample M (mutant strain MRJ-16) when compared to sample V (naive strain). Sample V (naive strain) protein annotations from previous step were used to annotate the SNP sites in the sample M (mutant strain MRJ-16) using the SnpEff software. The results of SNPs analysis is shown in table 3.

TABLE 3

SNPs analysis of mutant strain MRJ-16 and naive strain

| A #CHROM | B POS | C REF | D ALT | E QUAL | F | G | H | I |
|---|---|---|---|---|---|---|---|---|
| scaffold1 | size1605473 | 737632 | C | T | 221.999 | missense_variant | MODERATE | PCH03293.1 | Chromatin-remodelling complex, RSC SW |
| scaffold1 | size1605473 | 1001984 | C | A | 221.999 | upstream_gene_variant | MODIFIER | PCG95362.1 | Amidase |
| scaffold2 | size1468793 | 191909 | C | T | 221.999 | upstream_gene_variant | MODIFIER | PCG91910.1 | Succinate dehydrogenase, flavoprotein su |
| scaffold2 | size1468793 | 554756 | T | A | 221.999 | upstream_gene_variant | MODIFIER | PCH06707.1 | Heat shock protein DnaJ |
| scaffold2 | size1468793 | 1199260 | G | A | 221.999 | synonymous_variant | LOW | PCH07343.1 | Hypothetical protein PENO1_012430 |
| scaffold2 | size1468793 | 1199261 | A | T | 221.999 | missense_variant | MODERATE | PCH07343.1 | Hypothetical protein PENO1_012430 |

TABLE 3-continued

SNPs analysis of mutant strain MRJ-16 and naive strain

| A #CHROM | | B POS | C REF | D ALT | E QUAL | F | G | H | I |
|---|---|---|---|---|---|---|---|---|---|
| scaffold2 | size1468793 | 1298011 | A | T | 156.012 | upstream_gene_variant | MODIFIER | PCG90448.1 | Hypothetical protein PENO1_099160 |
| scaffold2 | size1468793 | 1463248 | A | G | 221.999 | upstream_gene_variant | MODIFIER | PCG93125.1 | Phytanoyl-CoA dioxygenase |

A. Scaffold1_size1605473: Reference scaffold position in sample V.
B. POS: position at which the snp is present on the scaffold.
C. REF: allele present in reference sequence of sample V.
D. ALT: alternative allele present in the sample M.
E. QUAL: quality value of the SNP position.
F. Type of the SNP: missense_variant, upstream_gene_variant, to name a few.
G. Effect of the SNP: Moderate, Modifier, High, Low.
H. GenBank Protein Id.
I. Putative Protein Annotation.

Example 5

Enzyme Production Efficiency of Mutant Strain MRJ-16 and Naive Strain

Fermentation process was carried out in aerated stirred tank bioreactor of 2 L glass jacketed vessel, with 1.8 L working volume. The media components of fermentation media used were ammonium sulphate 5 g/L, $KH_2PO_4$ 6 g/L, $MgSO_4.7H_2O$ 1 g/L, $CaCO_3$ 5 g/L, Glycerol 2.5 g/L, Corn steep solids 27 g/L, cellulose 30 g/L and Tween-80 2 ml/L. The fermenter containing 1.5 L medium was sterilized at 120° C. for 20 min. After cooling, the temperature was kept at 30° C., pH adjusted to 5.5 and inoculated with 10% active liquid seed (seed media composition in table 4) of *Penicillium* mutant strain. After 96 hours of fermentation, the enzyme broth was collected, centrifuged and analysis of clear enzyme broth was done.

TABLE 4

Seed/Inoculum Media composition

| S. No. | Chemical Components | Quantity (g/L) |
|---|---|---|
| 1 | Ammonium Sulphate | 4 |
| 2 | $KH_2PO_4$ | 3 |
| 3 | $MgSO_4 \cdot 7H_2O$ | 0.1 |
| 4 | $CaCO_3$ | 2 |
| 5 | Sucrose | 5 |
| 6 | Corn Steep Liquor | 15 |
| 7 | Cellulose | 10 |
| 8 | Tween-80 | 2 |
| 9 | pH | 5.5 |

The results obtained after 96 hours of incubation were that parent strain produces 8.5 g/L of protein, 22 IU/ml of β-glucosidase and 3.8 FPU/ml of filter paper activity, while MRJ-16 produces 15 g/L of protein, 62 IU/ml of β-glucosidase and 6.4 FPU/ml of filter paper activity. Hence, the mutant strain MRJ 16 possesses significantly enhanced enzyme production in comparison to parent strain.

Example 6

Enzyme Production Efficiency of Mutant Strain MRJ-16 and Naive Strain

Fermentation process was carried out in aerated stirred tank bioreactor of 2 L glass jacketed vessel, with 1.8 L working volume. The media components of fermentation media used were ammonium sulphate 3.5 g/L, $KH_2PO_4$ 4 g/L, $MgSO_4.7H_2O$ 0.5 g/L, $CaCO_3$ 2.5 g/L, Glycerol 2.5 g/L, Corn steep solids 20 g/L, cellulose 20 g/L and Tween-80 2 ml/L. The fermenter containing 1.5 L medium was sterilized at 120° C. for 20 min. After cooling, the temperature was kept at 30° C., pH adjusted to 5.5 and inoculated with 10% active liquid seed (seed media composition in table 5) of *Penicillium* MRJ-16 mutant strain. After 96 hours of fermentation, the enzyme broth was collected, centrifuged and analysis of clear enzyme broth was done.

TABLE 5

Seed/Inoculum Media composition

| S. No. | Chemical Components | Quantity (g/L) |
|---|---|---|
| 1 | Ammonium Sulphate | 5 |
| 2 | $KH_2PO_4$ | 6 |
| 3 | $MgSO_4 \cdot 7H_2O$ | 1 |
| 4 | $CaCO_3$ | 2.5 |
| 5 | Sucrose | 10 |
| 6 | Corn Steep Liquor | 10 |
| 7 | Cellulose | 20 |
| 8 | Tween-80 | 2 |
| 9 | pH | 5.5 |

The results obtained after 96 hours of incubation were naive strain produces 7.8 g/L of protein, 21 IU/ml of β-glucosidase and 3.4 FPU/ml of filter paper activity, while MRJ-16 produces 16.2 g/L of protein, 64 IU/ml of β-glucosidase and 6.2 FPU/ml of filter paper activity. Hence, the titer of enzyme produced using mutant strain MRJ 16 is at least two fold higher than enzyme produced using naive strain in fermentation process.

Example 7

Enzyme Production in the Presence of Glucose

In order to demonstrate the glucose repression on enzyme production, cellulose used as carbon source was replaced with glucose. Enzyme production from *Penicillium funiculosum* MRJ-16 mutant strain was carried out under the conditions and media composition as described in Examples 3 and 5 except cellulose. Concentrated solution of glucose was autoclaved separately and added into media at 3% w/v concentration. Fermentation was lasted approximately for about 120 hours, enzyme harvested and results analyzed are shown in below mentioned Table 6.

TABLE 6

Enzyme production from MRJ-16 and parent strain in the presence of glucose

| Fungal strain | Carbon Source Concentration (% w/v) | FPU/ml | BGL (IU/ml) |
|---|---|---|---|
| Penicillium funiculosum NCIM 1228 (Parent strain) | Cellulose 3% | 3.5 | 22.1 |
|  | Glucose 3% | 0.01 | 0 |
| Penicillium funiculosum MRJ-16 mutant | Cellulose 3% | 6.47 | 62 |
|  | Glucose 3% | 1.39 | 21 |

Example 8

Diversity of Enzyme Secreted

Cellulases enzymes production using *Penicillium funiculosum* MRJ-16 mutant strain was performed according to Example 5. The secretome analyses were done it is comprise enzyme activities of β-glucosidase 62 IU/ml, Filter paper activity 6.4 FPU/ml, endoglucanase 98 IU/ml, α-L arabinofuranosidase 0.02 IU/ml, β-xylosidase 0.5 IU/ml, xylanase 212 IU/ml, pectinase 97 IU/ml and oxidases 5.04 IU/ml analyzed using respective substrates.

Example 9

Diversity of Enzyme Secreted

Cellulases enzymes production using *Penicillium funiculosum* MRJ-16 mutant strain was performed according to example no. 6. The secretome analyses were done it is comprise enzyme activities of β-glucosidase 64 IU/ml, Filter paper activity 6.2 FPU/ml, endoglucanase 92 IU/ml, α-L arabinofuranosidase 0.02 IU/ml, β-xylosidase 0.7 IU/ml, xylanase 235 IU/ml, pectinase 82 IU/ml and oxidases 4.65 IU/ml analyzed using respective substrates.

Example 10

Hydrolysis of Pre-Treated Lignocellulosic Biomass Using Concentrated Enzyme

The efficiency of enzyme produced was determined by its ability to hydrolyze lignocellulosic biomass such as acid pretreated rice straw and produce sugars. Enzyme was first separated from fungal mycelia by centrifugation and clear broth was concentrated and used. Hydrolysis was performed at high substrate loading of biomass i.e. 20% at pH 4-5, 50 mM citrate buffer, temperature 50° C. at enzyme loadings of 6 FPU/g of dry biomass. Sugars released were determined at regular interval of time by HPLC. Enzyme cocktail worked efficiently and leads to 60% glucan conversion in 48 hours.

Example 11

Hydrolysis of Pre-Treated Lignocellulosic Biomass Using Enzyme as Such

The efficiency of enzyme produced was determined by its ability to hydrolyze lignocellulosic biomass such as acid pretreated rice straw and to produce sugars. Enzyme broth was used as such without any downstream processing. Hydrolysis was performed at high substrate loading of biomass i.e. 20% at pH 4-5, 50 mM citrate buffer, temperature 50° C. at enzyme loadings of 6 FPU/g of dry biomass. Sugars released were determined at regular interval of time by HPLC. Enzyme cocktail worked efficiently and leads to 60% glucan conversion in 48 hours.

The invention claimed is:

1. A mutant fungal strain, wherein the mutant fungal strain is *Penicillium funiculosum* MRJ 16, having Microbial Type Culture Collection (MTCC) Accession Number 25142, wherein the mutant fungal strain is characterized by the ability to produce at least two fold higher titer of an enzyme mixture comprising filter paper enzyme, carboxymethyl cellulase, Cellobiase, β-glucosidase, endoglucanase, α-L arabinofuranosidase, β-xylosidase, xylanase, pectinase, cellobiohydrase and oxidases as compared to a native *Penicillium funiculosum* NCIM 1228 strain; and wherein the mutant fungal strain has decreased carbon catabolite repression as compared to the native *Penicillium funiculosum* NCIM 1228 strain.

2. The mutant fungal strain of claim 1, wherein the enzyme mixture comprises cellulase and β-glucosidase.

3. The mutant fungal strain of claim 1, wherein a carbon catabolite repressor is glucose and/or xylose.

4. A method of preparing the mutant fungal strain of claim 1, the method comprising:
(i) subjecting the native *Penicillium funiculosum* NCIM 1228 strain to aerobic culture media to prepare a spore suspension of $1 \times 10^6$ spore/mL;
(ii) mutating the spore suspension by chemical mutagenesis followed by physical mutagenesis to produce mutant colonies;
(iii) screening the mutant colonies for cellulolytic activity using screening media comprising amorphous cellulose in a concentration of 0.1%-2% (w/w) and glucose in a concentration of 0.1-4% (w/w); and
(iv) obtaining the mutant fungal strain *Penicillium funiculosum* MRJ 16;
wherein:
the chemical mutagenesis is carried out with ethyl methanesulfonate (EMS) or diethyl sulfate (DES) in concentration of 10-50 μL/mL spore suspension or with both EMS and DES in 1:1 concentration for 15 hours under dark at room temperature, and the physical mutagenesis is carried out with UV light of wavelength 254 nm for 2-5 minutes at a distance of 15 cm.

5. A process for the producing cellulase enzymes, wherein the process comprises:
culturing the mutant fungal strain of claim 1 in a culture medium comprising a carbon source selected from the group consisting of rice straw, wheat straw, baggase, and a mixture thereof; and
collecting the cellulase enzymes from the culture medium.

6. A method for degrading or saccharifying a biomass, wherein the method comprises:
culturing the mutant fungal strain of claim 1 in a culture medium to produce cellulase enzymes;
hydrolysing pre-treated biomass with the cellulase enzymes, wherein the biomass is selected from the group consisting of rice straw, wheat straw, baggase, and a mixture thereof; and
obtaining products of degradation or saccharification, wherein the products are sugars.

* * * * *